US012584927B2

(12) United States Patent
Basmajian et al.

(10) Patent No.: US 12,584,927 B2
(45) Date of Patent: Mar. 24, 2026

(54) DIGITAL MICROFLUIDICS MULTI-DYNAMIC RANGE PARALLEL BIOCHEMICAL ASSAYS

(71) Applicant: Baebies, Inc., Durham, NC (US)

(72) Inventors: Michael A. Basmajian, Durham, NC (US); Michael Boso, Durham, NC (US); Jennifer Elderbroom, Durham, NC (US)

(73) Assignee: Baebies, Inc., Durham, NC (US)

( * ) Notice: Subject to any disclaimer, the term of this patent is extended or adjusted under 35 U.S.C. 154(b) by 836 days.

(21) Appl. No.: 17/962,898

(22) Filed: Oct. 10, 2022

(65) Prior Publication Data

US 2023/0288435 A1      Sep. 14, 2023

Related U.S. Application Data

(63) Continuation of application No. PCT/US2022/046076, filed on Oct. 7, 2022.

(60) Provisional application No. 63/350,233, filed on Jun. 8, 2022, provisional application No. 63/253,825, filed on Oct. 8, 2021.

(51) Int. Cl.
*G01N 33/72* (2006.01)
*B01L 3/00* (2006.01)

(52) U.S. Cl.
CPC ...... *G01N 33/728* (2013.01); *B01L 3/502792* (2013.01); *B01L 2400/0427* (2013.01)

(58) Field of Classification Search
None
See application file for complete search history.

(56) References Cited

U.S. PATENT DOCUMENTS

| | | | |
|---|---|---|---|
| 6,582,662 | B1 | 6/2003 | Kellogg et al. |
| 2005/0136400 | A1 | 6/2005 | Lin et al. |
| 2011/0143414 | A1 | 6/2011 | Cho et al. |

(Continued)

FOREIGN PATENT DOCUMENTS

EP      1436620 B1 *  4/2014   ....... G01N 33/56944

OTHER PUBLICATIONS

Sista Rama S. et al: "Digital Microfluidic Platform to Maximize Diagnostic Tests with Low Sample Volumes from Newborns and Pediatric Patients", Diagnostics, vol. 10, No. 1, Jan. 1, 2020 (Jan. 1, 2020), p. 21.

(Continued)

*Primary Examiner* — Matthew D Krcha
(74) *Attorney, Agent, or Firm* — E. Eric Mills; Nicholas P. Stadnyk; Maynard Nexsen PC

(57) ABSTRACT

The invention relates generally to biochemical assays and more particularly to digital microfluidics multi-dynamic range parallel biochemical assays. The invention provides methods that enable improved precision and linearity for digital microfluidics analyses (i.e., analyses performed on a droplet actuator using droplet operations), including for example, assays related to measuring analytes in a biological sample. Examples of assays that may be performed using a method of the invention include measuring analytes in blood, including analytes from blood components, such as analytes present in plasma. The invention provides a digital microfluidics device (or cartridge) and methods for performing a biochemical assay using the microfluidics device to measure an analyte in a sample.

29 Claims, 8 Drawing Sheets

(56) References Cited

U.S. PATENT DOCUMENTS

| 2016/0238595 | A1   | 8/2016  | Herr et al. |
| 2019/0154678 | A1 * | 5/2019  | Pamula ............ G01N 33/54366 |
| 2019/0317085 | A1   | 10/2019 | Griffiths et al. |

OTHER PUBLICATIONS

Harris Leanne F. et al: "A microfluidic anti-Factor Xa assay device for point of care monitoring of anticoagulation therapy", Analyst, vol. 138, No. 17, Sep. 7, 2013 (Sep. 7, 2013), pp. 4769-4776.
David Millington et al: "Digital microfluidics comes of age: high-throughput screening to bedside diagnostic testing for genetic disorders in newborns", Expert Reviews in Molecular Diagnostics, vol. 18, No. 8, Aug. 3, 2018 (Aug. 3, 2018), pp. 701-712.

* cited by examiner

200

212

214

220        218

216

210

300

600

Diluent
reservoir 610

R3    R2    R1
Reagent reservoirs 615

Sample
reservoir
625

DIGITAL MICROFLUIDICS MULTI-DYNAMIC RANGE PARALLEL BIOCHEMICAL ASSAYS

CROSS-REFERENCE TO RELATED APPLICATIONS

This application is a 35 U.S.C. § 111(a) U.S. bypass continuation application of International Application No. PCT/US2022/46076 having an international filing date of Oct. 7, 2022, which claims priority to U.S. Patent App. No. 63/253,825, entitled "Digital Microfluidics Multi-Dynamic Range Parallel Biochemical Assays," filed on Oct. 8, 2021; and U.S. Patent App. No. 63/350,233, entitled "Digital Microfluidics Multi-Dynamic Range Parallel Biochemical Assays," filed on Jun. 8, 2022; the entire disclosures of which are incorporated herein by reference.

GOVERNMENT RIGHTS IN THE INVENTION

This invention was made with government support under Grant No. R44HL140662 and Grant No. R44HL146016 awarded by the National Institutes of Health (NIH). The government has certain rights in the invention.

FIELD OF THE INVENTION

The invention relates generally to biochemical assays and more particularly to digital microfluidics multi-dynamic range parallel biochemical assays.

BACKGROUND OF THE INVENTION

Digital microfluidics technology is used to perform a variety of assay types, such as biochemical assays to measure the amount of an analyte in a sample. For example, a digital microfluidics assay for quantifying the amount of analyte in a sample typically involves performing a reaction that produces a detectable signal and translating that signal into a measure of the amount of analyte present in the sample. However, conducting biochemical assays on a microfluidics device introduces unique issues as well as opportunities for improving upon currently available analytical techniques.

SUMMARY OF THE EXEMPLARY EMBODIMENTS

In one embodiment, a method is provided for assaying analytes on a microfluidic device. The method includes: (a) loading a sample including an analyte to be assayed onto a microfluidic device; (b) merging a first droplet of the sample with one or more reaction reagents for a short-incubation reaction to measure a relatively high concentration range of the analyte and performing the short-incubation reaction protocol, wherein a first relatively high concentration range negative-slope standard curve is used for quantifying the analyte; (c) merging a second droplet of the sample with the one or more reaction reagents for a long-incubation of the reaction in (b) to measure a relatively low concentration range of the analyte and performing the long-incubation reaction protocol, wherein a second relatively low concentration range negative-slope standard curve is used for quantifying the analyte; and (c) calculating a concentration of the analyte by comparing the results of the short- and long-incubation reactions that were performed.

Optionally, the method can further include merging one or more additional droplets of the sample with one or more reaction reagents for one or more relatively shorter, longer, or intermediate incubations of the reaction in (b) to measure one or more relatively shorter, longer, or intermediate concentration ranges of the analyte and performing the relatively shorter, longer, or intermediate reaction protocol, wherein a third relatively shorter, longer, or intermediate concentration range negative-slope standard curve is used for quantifying the analyte.

In some instances, the assay is an enzyme inhibition assay and the measured signal decreases as the concentration of the analyte increases.

In other cases, the assay is an assay for degradation of the analyte, or measures degradation of the analyte.

In one example, the sample is a whole blood sample, the assay is an enzyme inhibition assay, and the analyte is heparin. The one or more reaction reagents can include an FXa enzyme reagent and an FXa-specific substrate, and a plasma sample droplet from the whole blood sample can be (1) merged with the FXa enzyme reagent and then (2) the combined blood sample-enzyme reagent droplet cam be merged with the FXa-specific substrate. In addition, the step (1) and step (2) can be reversed. The FXa-specific substrate can be a chromogenic substrate or a fluorogenic substrate.

In the method for assaying analytes on a microfluidic device, the sample can be a blood sample and a plasma sample droplet can be prepared from the whole blood sample on the microfluidic device. The preparing can include combining a whole blood sample droplet with an agglutination reagent and separating the plasma fraction from the red blood cell fraction using a plasma separation process. In other instances, the plasma sample is prepared from the whole blood sample prior to loading onto the microfluidic device.

In some embodiments, the analyte is heparin, which can be unfractionated heparin (UFH) or low molecular weight heparin (LMWH).

In one instance, performing the short-incubation reaction protocol includes: (a) dispensing a one (1) droplet unit (DU) (1DU) of the plasma sample and transporting it to a reaction and detection zone; (b) dispensing a 1DU of the FXa enzyme reagent and merging it with the IDU plasma sample droplet to yield a 2DU short reaction droplet; (c) mixing the 2DU short reaction droplet; (d) dispensing a 1DU of the fluorogenic FXa-specific substrate reagent and combining it with the 2DU short reaction droplet to yield a 3DU short detection droplet; and (c) mixing the 3DU short detection droplet and reading relative activity units over time as a measured signal for the short-incubation reaction.

In this instance, the method can further include performing a washing protocol to clean the reaction and detection zone after the short-incubation reaction protocol. Next, the long-incubation reaction protocol includes: (a) dispensing a 1DU of the plasma sample and merging it with a 1DU of FXa enzyme reagent to yield a 2DU long reaction droplet; (b) mixing the 2DU long reaction droplet; (c) dispensing a 1DU of the fluorogenic FXa-specific substrate reagent and combining it with the 2DU long reaction droplet to yield a 3DU long detection droplet; and (d) mixing the 3DU long detection droplet and reading relative activity units over time as the measured signal for the long-incubation reaction.

In one example, the sample is a blood sample, the assay is an assay for degradation of the analyte (or measures degradation of the analyte), and the analyte is unbound bilirubin.

In various embodiments of the method for assaying analytes on a microfluidic device, the microfluidic device can include an electrowetting cartridge and the loading, merging, combining, dispensing, and/or initiating can be performed using electrowetting-mediated droplet operations.

In one instance, a method of measuring heparin in a plasma droplet is provided that includes: (a) providing two or more plasma droplets for a fluorescence-based anti-Factor Xa ("anti-FXa") assay to measure heparin concentration using electrowetting-mediated droplet operations to perform assay steps; (b) initiating a short-incubation reaction of the assay to measure a relatively high concentration range of heparin in one or more of the two or more sample droplets; (c) initiating a long-incubation reaction of the assay to measure a relatively low concentration range of heparin in one or more of the two or more sample droplets; and (d) calculating a concentration of heparin using a separate negative-slope standard curve for each of the concentration ranges of heparin measured in the method.

In another example, a method is provided for measuring analytes in a blood sample that includes using electrowetting-mediated droplet operations on a microfluidic device. The method includes: (i) dispensing two or more sample droplets from a blood sample or a diluted blood sample in a droplet operations gap of the microfluidic device, (ii) initiating a short-incubation biochemical assay to measure a relatively high concentration range of an analyte in one or more of the two or more sample droplets, wherein a first relatively high concentration range negative-slope standard curve is used for quantifying the analyte; and (iii) initiating a long-incubation of the biochemical assay of (ii) to measure a relatively low concentration range of the analyte in one or more of the two or more sample droplets, wherein a second relatively low concentration range negative-slope standard curve is used for quantifying the analyte. Using a computer, calculating a concentration of the analyte by comparing the results of the short- and long-incubation reactions that were performed.

In some instances, the method includes performing one or more incubation reactions that are shorter, longer, or of intermediate duration relative to the short- and long-incubation reactions.

In various embodiments of the methods provided herein, the analyte or the heparin includes unfractionated heparin (UFH) or low molecular weight heparin (LMWH).

In the methods, the biochemical assay can include an enzyme inhibition assay where the measured signal decreases as the concentration of the analyte increases, or the biochemical assay can include an assay for degradation of the analyte (e.g., measuring degradation of the analyte). The assay can be an absorbance-based assay, a luminescence-based assay or a fluorescence-based assay.

In the disclosed methods, the sample can be whole blood, plasma, or serum.

The incubation reactions can be run in parallel on the microfluidic device or run one after the other on the microfluidic device. The incubation reactions can be individually tuned to improve one or both precision and linearity in the assay. The tuning can include optimizing one or a combination of: (a) length of the incubation reaction; (b) a concentration of one or more of the reagents; and (c) a dilution of the sample. In some instances, the incubation reactions are performed in a reaction and detection zone on the microfluidic device, and the method further includes performing a washing protocol to clean the reaction and detection zones between incubation reactions.

In various embodiments, one or more of the reaction reagents is provided as a dried reagent spot on one or more droplet operations electrodes on the microfluidic device. The one or more dried reagent spots can be rehydrated using a diluent solution provided in a diluent reservoir.

In other embodiments, a system is provided. The system includes a computer processor and an electrowetting cartridge. The processor is programmed to execute one or more of the methods provided herein.

In another embodiment, a kit is provided. The kit includes an electrowetting cartridge and reagents sufficient to execute one or more of the methods provided herein.

In one aspect, the present disclosure is directed to a method for assaying analytes on a microfluidic device, the method comprising: (a) loading a sample comprising an analyte to be assayed onto a microfluidic device; (b) performing a short-incubation reaction protocol to measure a relatively high concentration of the analyte, the short-incubation reaction protocol comprising merging a first droplet of the sample with one or more reaction reagents, wherein the short-incubation reaction protocol is optimized to measure a relatively high concentration of the analyte, and wherein a first relatively high concentration range negative-slope standard curve is used for quantifying the analyte; (c) performing a long incubation reaction protocol to measure a relatively low concentration of the analyte, the long incubation reaction protocol comprising merging a second droplet of the sample with the one or more reaction reagents, wherein the long incubation reaction protocol is optimized to measure a relatively low concentration of the analyte, and wherein a second relatively low concentration range negative-slope standard curve is used for quantifying the analyte; (d) optionally, performing an intermediate incubation reaction protocol to measure an intermediate concentration of the analyte, the intermediate incubation reaction protocol comprising merging a third droplet of the sample with one or more reaction reagents, wherein the intermediate reaction protocol is optimized to measure an intermediate concentration of the analyte, and wherein a third intermediate concentration range negative-slope standard curve is used for quantifying the analyte; and (e) calculating a concentration of the analyte using the high concentration range negative-slope standard curve, the low concentration range negative-slope standard curve, and/or optionally the intermediate negative-slope standard curve.

In some embodiments, calculating the concentration of the analyte comprises comparing the calculated concentration of the analyte from the high concentration range negative-slope standard curve and the calculated concentration of the analyte from the low concentration range negative-slope standard curve, and optionally the calculated concentration of the analyte from the intermediate negative-slope standard curve.

In some embodiments, calculated concentrations from the high concentration range negative-slope standard curve, from the low concentration range negative-slope standard curve, and optionally from the calculated concentration of the analyte from the intermediate negative-slope standard curve, are combined using weighted averages.

In some embodiments, the protocols of the assay (e.g., the short-, long, and optionally intermediate incubation reaction protocols) comprise an enzyme inhibition assay wherein the measured signal decreases as the concentration of the analyte increases. In some embodiments, the protocols of the assay comprise an assay for degradation of the analyte or for measuring degradation of the analyte.

In some embodiments, the sample is whole blood, plasma or serum. In some embodiments, the sample is a blood sample. In some embodiments, the sample is a plasma sample and the plasma sample is prepared from a whole blood sample on the microfluidic device.

In some embodiments, the one or more reaction reagents includes an analyte-specific substrate, and wherein the substrate is a chromogenic substrate or a fluorogenic substrate. In some embodiments, the protocols of the assay comprise an absorbance-based assay, a luminescence-based assay or a fluorescence-based assay.

In some embodiments, the sample is a whole blood sample, the protocols of the assay comprise an enzyme inhibition assay, and the analyte is heparin.

In some embodiments, the one or more reaction reagents comprises an FXa enzyme reagent and an FXa-specific substrate, and wherein a plasma sample droplet from the whole blood sample is (1) merged with the FXa enzyme reagent and then (2) the combined blood sample-enzyme reagent droplet is merged with the FXa-specific substrate, or wherein step (1) and step (2) are reversed.

In some embodiments, the FXa-specific substrate is a chromogenic substrate, a luminescence substrate, or a fluorogenic substrate and wherein the protocols of the assay comprise an absorbance-based assay, a luminescence-based assay, or a fluorescence-based assay.

In some embodiments, the preparing comprises combining a whole blood sample droplet with an agglutination reagent and separating a plasma fraction from a red blood cell fraction using a plasma separation process. In some embodiments, the plasma sample is prepared from the whole blood sample prior to loading onto the microfluidic device.

In some embodiments, the heparin is unfractionated heparin (UFH) or low molecular weight heparin (LMWH).

In some embodiments, performing the short-incubation reaction protocol comprises: (a) dispensing a one (1) droplet unit (DU) (1DU) of the plasma sample and transporting it to a reaction and detection zone; (b) dispensing a 1DU of the FXa enzyme reagent and merging it with the 1DU plasma sample droplet to yield a 2DU short reaction droplet; (c) mixing the 2DU short reaction droplet; (d) dispensing a 1DU of the fluorogenic FXa-specific substrate reagent and combining it with the 2DU short reaction droplet to yield a 3DU short detection droplet; and (e) mixing the 3DU short detection droplet and reading relative activity units over time as a measured signal for the short-incubation reaction.

In some embodiments, the method further comprising performing a washing protocol to clean the reaction and detection zone, and wherein the long-incubation reaction protocol comprises: (a) dispensing a 1 DU of the plasma sample and merging it with a 1DU of FXa enzyme reagent to yield a 2DU long reaction droplet; (b) mixing the 2DU long reaction droplet; (c) dispensing a 1DU of the fluorogenic FXa-specific substrate reagent and combining it with the 2DU long reaction droplet to yield a 3DU long detection droplet; and (d) mixing the 3DU long detection droplet and reading relative activity units over time as the measured signal for the long-incubation reaction.

In some embodiments, the sample is a blood sample, the protocols of the assay comprise an assay for degradation of the analyte, and the analyte is unbound bilirubin.

In some embodiments, the microfluidic device comprises an electrowetting cartridge and the loading, merging, combining, dispensing, and/or initiating is performed using electrowetting-mediated droplet operations.

In some embodiments, the incubation reactions are individually tuned to improve one or both precision and linearity in the assay. In some embodiments, tuning comprises optimizing one or a combination of: (a) length of the incubation reaction; (b) a concentration of one or more of the reagents; and (c) a dilution of the sample.

In some embodiments, the incubation reactions are run in parallel on the microfluidic device or run one after the other on the microfluidic device.

In some embodiments, the incubation reactions are performed in a reaction and detection zone on the microfluidic device, the method further comprising performing a washing protocol to clean the reaction and detection zones between incubation reactions.

In some embodiments, the one or more of the reaction reagents are provided as a dried reagent spot on one or more droplet operations electrodes on the microfluidic device. In some embodiments, the one or more dried reagent spots are rehydrated using a diluent solution provided in a diluent reservoir.

In some embodiments, the short-incubation reaction protocol comprises an incubation period of less than about sixty (60) seconds. In other embodiments, the short incubation period can be from about 10 seconds to about 60 seconds, from about 30 seconds to about 60 seconds, or from about 45 seconds to about 60 seconds.

In some embodiments, the long incubation reaction protocol comprises an incubation period of more than about sixty (60) seconds. In other embodiments, the long incubation period can be from about 60 seconds to about 240 seconds, from about 60 seconds to about 180 seconds, or from about 60 seconds to about 120 seconds.

In some embodiments, the sample is a blood sample having an unbound bilirubin level of more than 2 mg/dL, the analyte-specific substrate is a fluorogenic substrate and the assay is a fluorescence-based assay. In some embodiments, the blood sample has a bilirubin level or more than 1 mg/dL, more than 2 mg/dL, more than 3 mg/dL, more than 4 mg/dL, or more than 5 mg/dL, the analyte-specific substrate is a fluorogenic substrate and the assay is a fluorescence-based assay. In some embodiments, the blood sample is from a neonate.

In another aspect, the present disclosure is directed to a method for assaying analytes on a microfluidic device, the method comprising: (a) loading a sample comprising an analyte to be assayed onto a microfluidic device; (b) performing a first reaction, wherein the first reaction comprises merging a first droplet of the sample with a first reaction droplet having a first reagent concentration optimized to measure a relatively high concentration of the analyte, and wherein a high concentration range negative-slope standard curve is used for quantifying the analyte in a high concentration range; (c) performing a second reaction, wherein the second reaction comprises merging a second droplet of the sample with a second reaction droplet having a second reagent concentration optimized to measure a relatively low concentration of the analyte, and wherein a low concentration range negative-slope standard curve is used for quantifying the analyte in a low concentration range; (d) optionally, performing a third reaction, wherein the third reaction comprises merging a third droplet of the sample with a third reaction droplet having a third reagent concentration optimized to measure an intermediate concentration of the analyte, and wherein an intermediate concentration range negative-slope standard curve is used for quantifying the analyte in an intermediate concentration range; (e) calculating a concentration of the analyte using the high concentration range negative-slope standard curve and/or the low concentration range negative-slope standard curve.

In some embodiments, calculating the concentration of the analyte comprises comparing the calculated concentration of the analyte from the high concentration range negative-slope standard curve and the calculated concentration of the analyte from the low concentration range negative-slope standard curve, and optionally the calculated concentration of the analyte from the intermediate negative-slope standard curve.

In some embodiments, the calculated concentrations from the high concentration range negative-slope standard curve, from the low concentration range negative-slope standard curve, and optionally from the calculated concentration of the analyte from the intermediate negative-slope standard curve, are combined using weighted averages.

In some embodiments, the reactions of the assay (e.g., the first, second, and optionally third reactions) comprise an enzyme inhibition assay wherein the measured signal decreases as the concentration of the analyte increases. In some embodiments, the reactions of the assay comprise an assay for degradation of the analyte or for measuring degradation of an analyte.

In some embodiments, the sample is whole blood, plasma or serum. In some embodiments, the sample is a blood sample. In some embodiments, the sample is a plasma sample and the plasma sample is prepared from a whole blood sample on the microfluidic device.

In some embodiments, the one or more reaction reagents includes an analyte-specific substrate, and wherein the substrate is a chromogenic substrate or a fluorogenic substrate. In some embodiments, the reactions of the assay comprise an absorbance-based assay, a luminescence-based assay, or a fluorescence-based assay.

In some embodiments, the sample is a whole blood sample, the reactions of the assay comprise an enzyme inhibition assay, and the analyte is heparin.

In some embodiments, the one or more reaction reagents comprises an FXa enzyme reagent and an FXa-specific substrate, and wherein a plasma sample droplet from the whole blood sample is (1) merged with the FXa enzyme reagent and then (2) the combined blood sample-enzyme reagent droplet is merged with the FXa-specific substrate, or wherein step (1) and step (2) are reversed.

In some embodiments, the FXa-specific substrate is a chromogenic substrate, a luminescence substrate, or a fluorogenic substrate and wherein the reactions of the assay comprise an absorbance-based assay, a luminescence-based assay or a fluorescence-based assay.

In some embodiments, the sample is a blood sample. In some embodiments, the sample is a plasma sample and the plasma sample is prepared from a whole blood sample on the microfluidic device.

In some embodiments, the heparin is unfractionated heparin (UFH) or low molecular weight heparin (LMWH).

In some embodiments, performing the first reaction protocol comprises: (a) dispensing a one (1) droplet unit (DU) (1DU) of the plasma sample and transporting it to a reaction and detection zone; (b) dispensing a 1DU of the FXa enzyme reagent, wherein the FXa enzyme reagent is at a first concentration optimized for a high concentration of heparin, and merging it with the IDU plasma sample droplet to yield a 2DU short reaction droplet; (c) mixing the 2DU short reaction droplet; (d) dispensing a 1DU of the fluorogenic FXa-specific substrate reagent and combining it with the 2DU reaction droplet to yield a 3DU detection droplet; and (e) mixing the 3DU short detection droplet and reading relative activity units over time as a measured signal for the first reaction protocol.

In some embodiments, the method further comprising performing a washing protocol to clean the reaction and detection zone, and wherein the second reaction protocol comprises: (a) dispensing a 1 DU of the plasma sample and merging it with a 1DU of FXa enzyme reagent, wherein the FXa enzyme reagent is at a second concentration optimized for a low concentration of heparin, to yield a 2DU long reaction droplet; (b) mixing the 2DU long reaction droplet; (c) dispensing a 1DU of the fluorogenic FXa-specific substrate reagent and combining it with the 2DU long reaction droplet to yield a 3DU long detection droplet; and (d) mixing the 3DU long detection droplet and reading relative activity units over time as the measured signal for the long-incubation reaction.

In some embodiments, the sample is a blood sample, the reactions of the assay comprise an assay for degradation of the analyte, and the analyte is unbound bilirubin.

In some embodiments, the microfluidic device comprises an electrowetting cartridge and the loading, merging, combining, dispensing, and/or initiating is performed using electrowetting-mediated droplet operations.

In some embodiments, the incubation reactions are individually tuned to improve one or both precision and linearity in the assay. In some embodiments, tuning comprises optimizing one or a combination of: (a) length of the incubation reaction; (b) a concentration of one or more of the reagents; and (c) a dilution of the sample.

In some embodiments, the incubation reactions are run in parallel on the microfluidic device or run one after the other on the microfluidic device. In some embodiments, the incubation reactions are performed in a reaction and detection zone on the microfluidic device, the method further comprising performing a washing protocol to clean the reaction and detection zones between incubation reactions.

In some embodiments, the one or more of the reaction reagents are provided as a dried reagent spot on one or more droplet operations electrodes on the microfluidic device. In some embodiments, the one or more dried reagent spots are rehydrated using a diluent solution provided in a diluent reservoir.

In some embodiments, the first reaction protocol includes an enzyme reagent at a concentration of less than about 0.5 U/mL. In other embodiments, the first reagent includes an enzyme reagent at a concentration of from about 0.01 U/mL to about 0.5 U/mL, from about 0.05 U/mL to about 0.5 U/mL, or from about 0.1 U/mL to about 0.5 U/mL.

In some embodiments, the second reaction protocol includes an enzyme reagent at a concentration of more than about 0.5 U/mL. In other embodiments, the first reagent includes an enzyme reagent at a concentration of from about 0.5 U/mL to about 1.5 U/mL, from about 0.75 U/mL to about 1.5 U/mL, or from about 1.0 U/mL to about 1.5 U/mL.

In some embodiments, the sample is a blood sample having an unbound bilirubin level of more than 2 mg/dL, the analyte-specific substrate is a fluorogenic substrate and the assay is a fluorescence-based assay. In some embodiments, the blood sample has a bilirubin level or more than 1 mg/dL, more than 2 mg/dL, more than 3 mg/dL, more than 4 mg/dL, or more than 5 mg/dL, the analyte-specific substrate is a fluorogenic substrate and the assay is a fluorescence-based assay. In some embodiments, the blood sample is from a neonate.

In another aspect, the present disclosure is directed to a system comprising a computer processor and an electrowetting cartridge wherein the processor is programmed to execute any of the methods described herein.

In still another aspect, the present disclosure is directed to a kit comprising an electrowetting cartridge and reagents sufficient to execute any of the methods described herein.

BRIEF DESCRIPTION OF THE DRAWINGS

Figure 1:
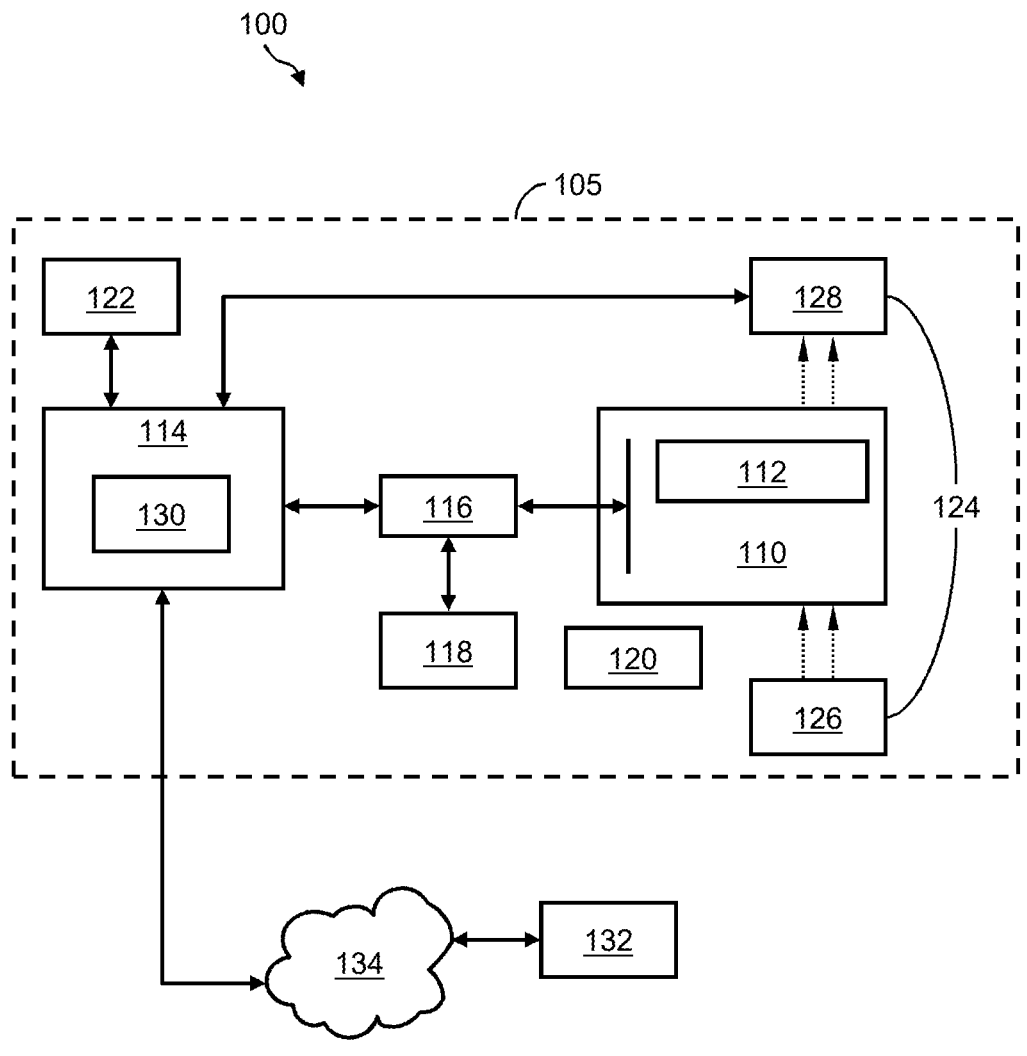

Having thus described the subject matter in general terms, reference will now be made to the accompanying drawings, which are not necessarily drawn to scale, and wherein:

FIG. 1 illustrates a simplified block diagram of an example of a microfluidics system for performing blood coagulation assays in droplets.

Figure 2:
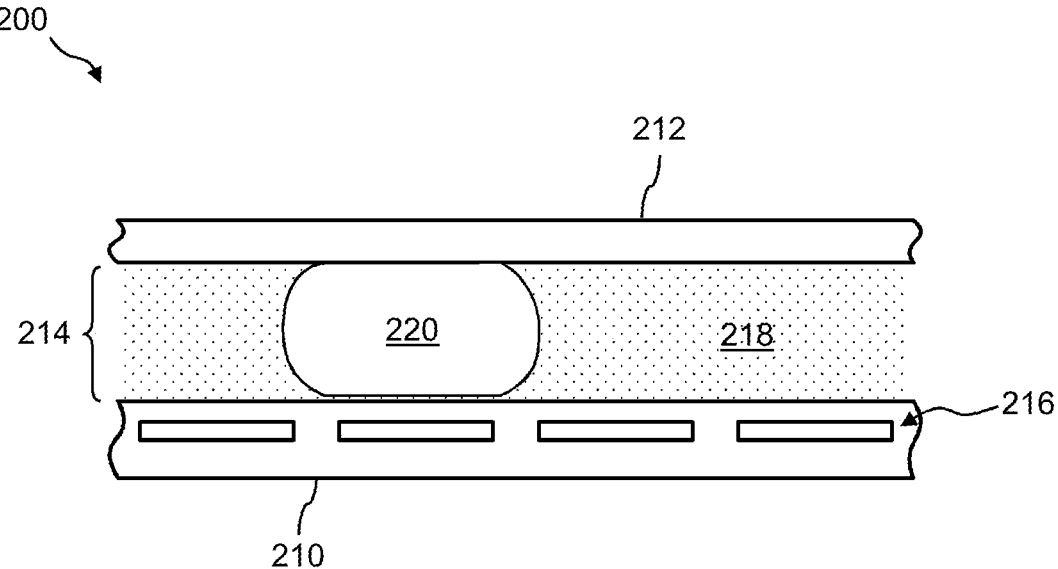

FIG. 2 is a cross-sectional view illustrating an example of a portion of a microfluidics device for performing a biochemical assay in droplets.

Figure 3:
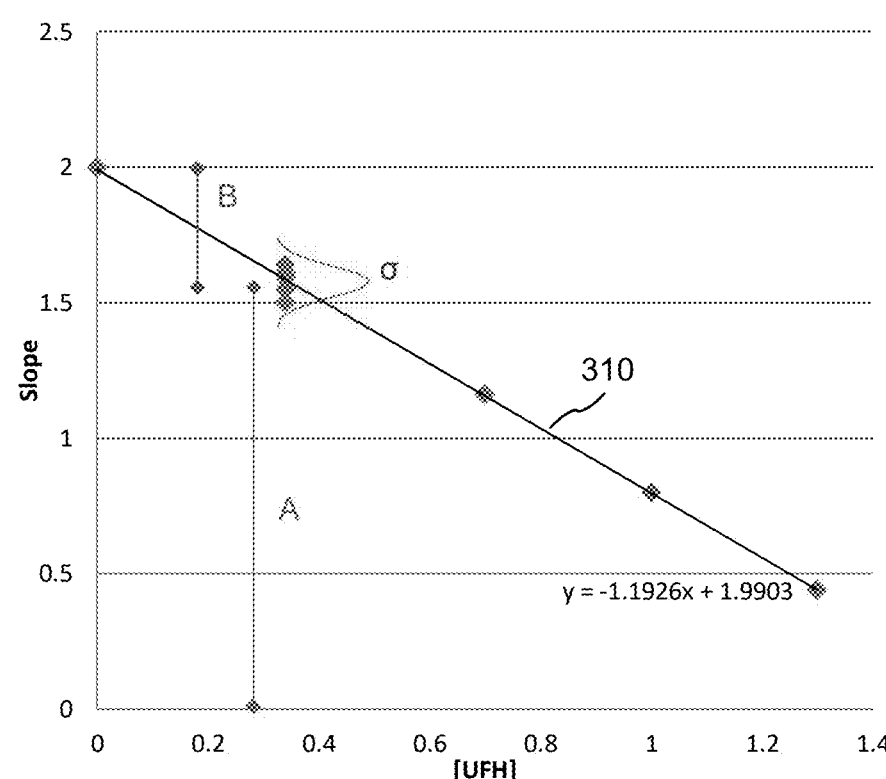

FIG. 3 is a plot showing an example of a standard curve for determining heparin (UFH) concentration in a sample.

Figure 4:
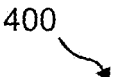
Figure 4:
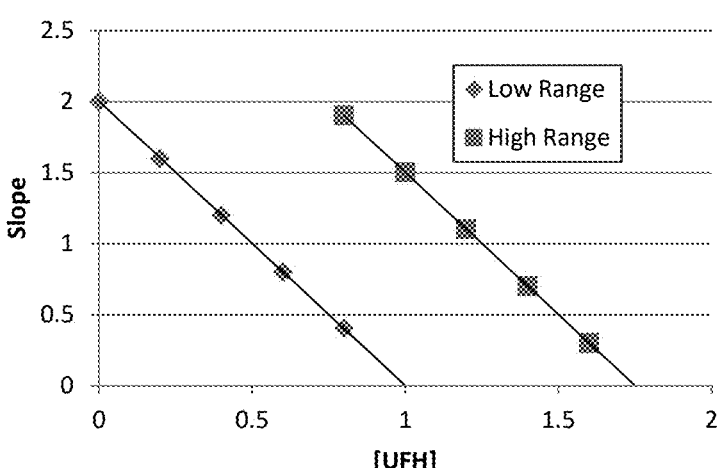

FIG. 4 is a plot showing an example of two separate standard curves tuned for quantification of a lower and a higher range of unfractionated heparin (UFH).

Figure 5:
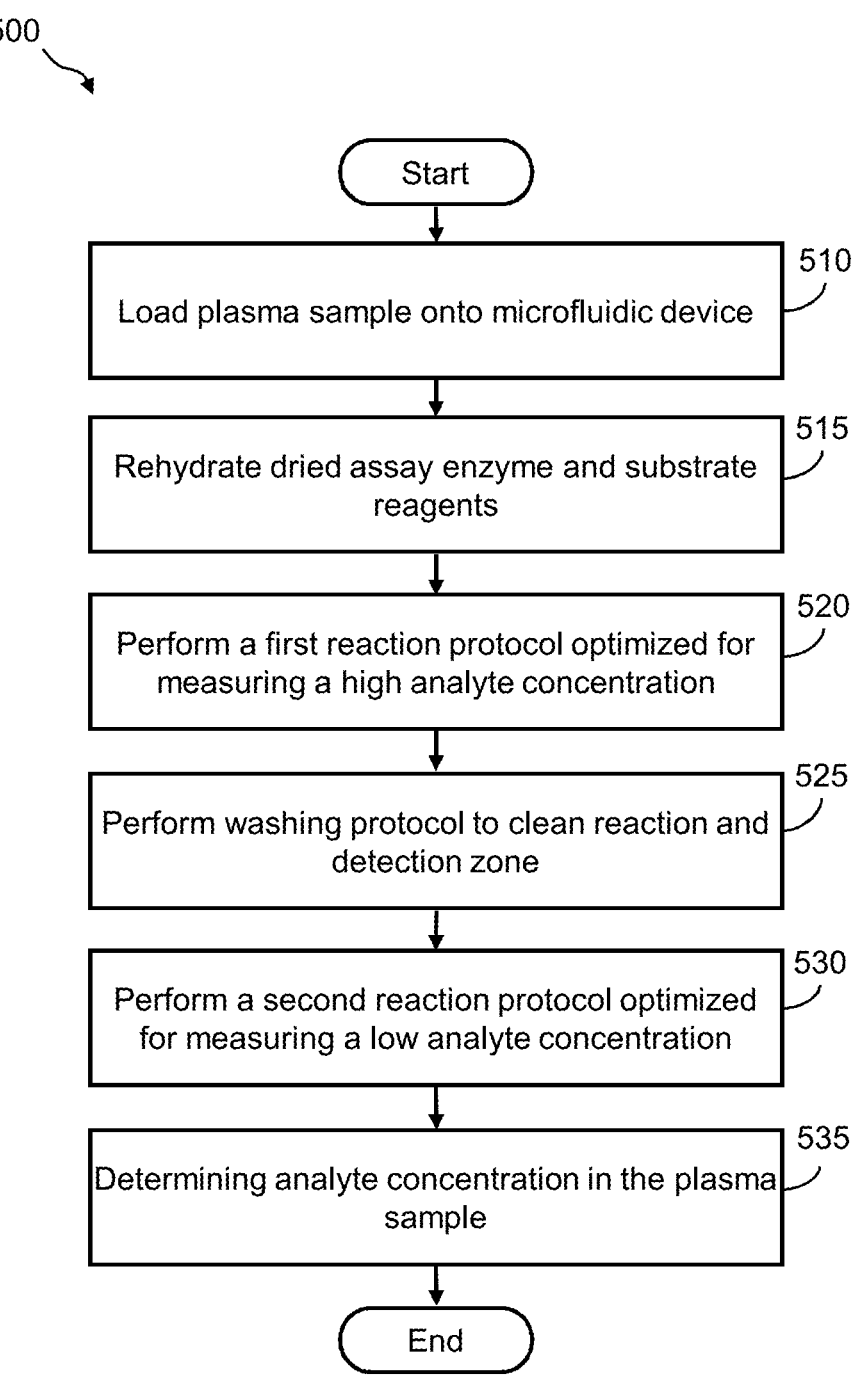

FIG. 5 is a flow diagram illustrating an example of a method for measuring an analyte in a test sample on a microfluidic device.

Figure 6:
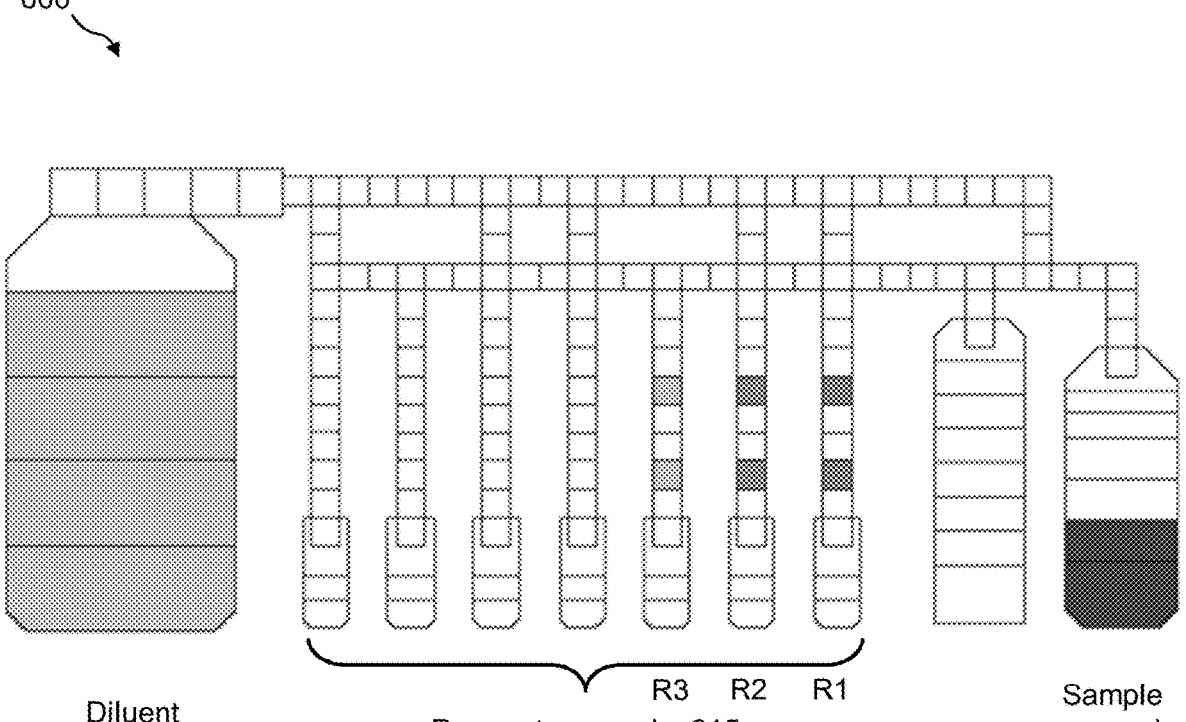

FIG. 6 is a schematic diagram illustrating an example of an arrangement of droplet operations electrodes configured for conducting an anti-FXa assay for heparin monitoring on a microfluidic device.

Figure 7:
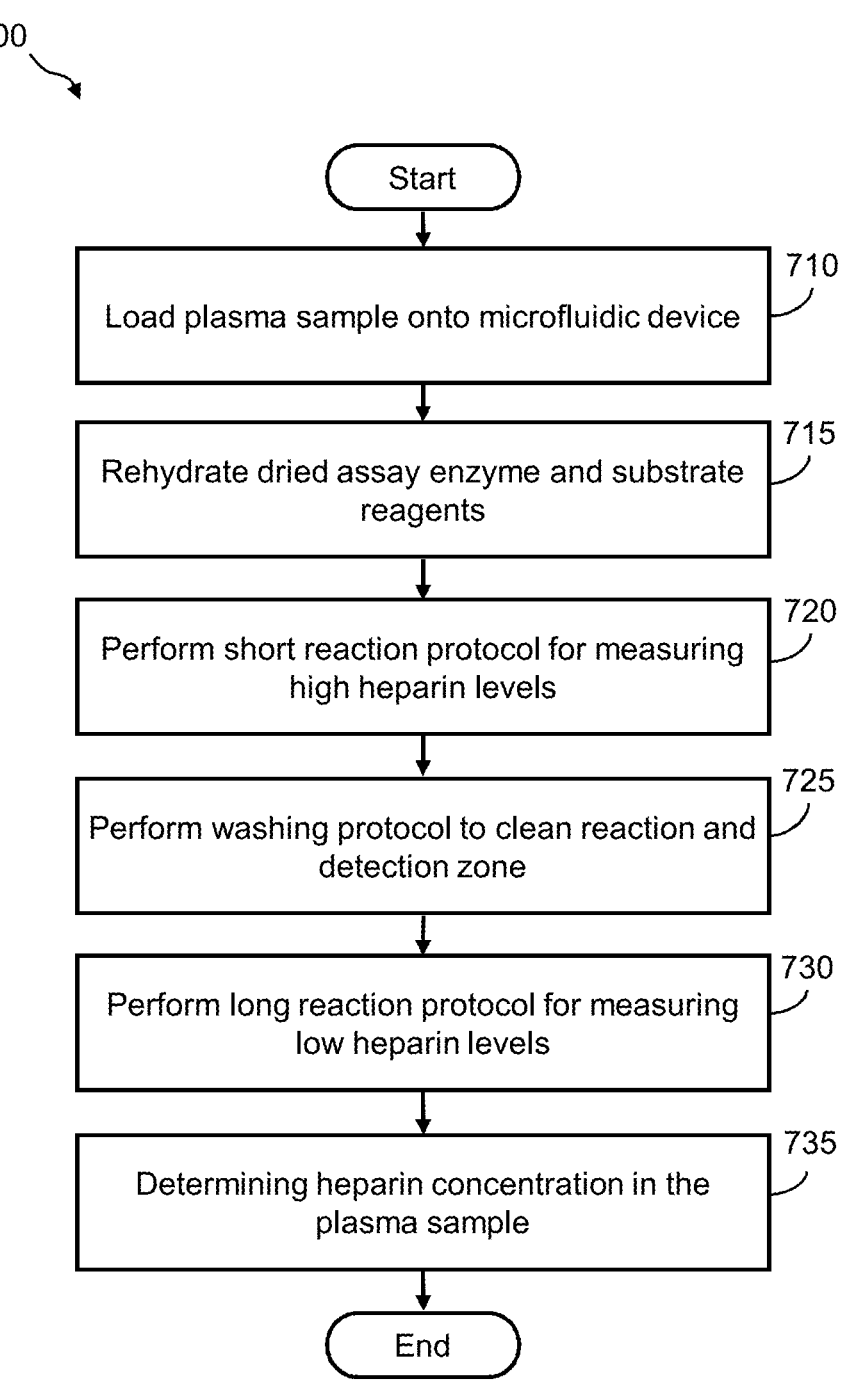

FIG. 7 is a flow diagram illustrating an example of a method for measuring heparin in a plasma sample using an anti-FXa assay on a microfluidic device.

Figure 8:
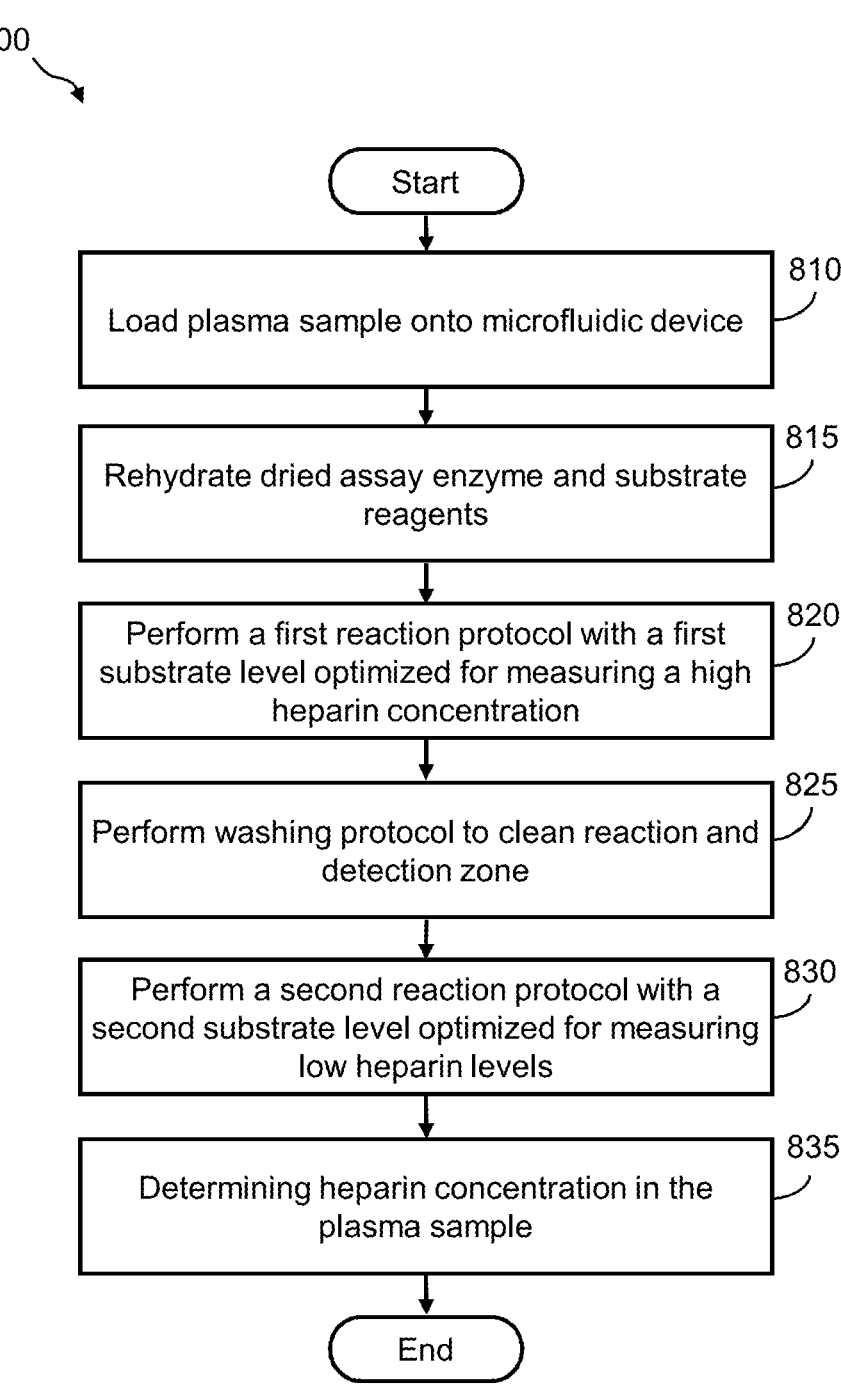

FIG. 8 is a flow diagram illustrating an example of a method for measuring heparin in a plasma sample using an anti-FXa assay on a microfluidic device.

DEFINITIONS

"Precision" refers to the closeness of repeated individual measurements of an analyte under specified conditions. The term may be used, for example, to describe the repeatability and reproducibility of an assay.

"Linearity" refers to the ability of an assay (test) to provide results that are directly proportional to the concentration of an analyte in a test sample.

DETAILED DESCIPTION

Microfluidic System, Device, and Methods

Fluidics systems and devices are used in a variety of applications to manipulate, process and/or analyze biological materials. Examples of fluidics devices include droplet actuators, microfluidics cartridges, digital microfluidics (DMF) devices, DMF cartridges, flow cell devices, and the like. The disclosure provides a microfluidic system, device, and methods including droplets subject to manipulation by the device wherein droplet movement is used to characterize coagulation of a blood sample.

Referring now to FIG. 1 is a simplified block diagram of an example of a microfluidics system 100 for performing one or more assays in droplets, in accordance with the present disclosure. In this example, microfluidics system 100 may include a fluidics instrument 105. Further, fluidics instrument 105 may house a microfluidics cartridge 110 along with any supporting components. Microfluidics cartridge 110 of microfluidics system 100 may be, for example, any fluidics device or cartridge, microfluidics device or cartridge, DMF device or cartridge, droplet actuator, flow cell device or cartridge, and the like. In various embodiments, microfluidics system 100 provides microfluidics cartridge 110 that may support automated processes to manipulate, process, and/or analyze biological materials.

Microfluidics cartridge 110 may be provided, for example, as a disposable and/or reusable device or cartridge. Microfluidics cartridge 110 may be used for processing biological materials. For example, one or more assays 112 may be executed on microfluidics cartridge 110 using, for example, droplet operations.

Also housed in fluidics instrument 105 of microfluidics system 100 may be a controller 114, a cartridge interface 116, certain thermal control electronics 118, one or more magnets 120, a graphical user interface (GUI) 122, and a detection system 124. Controller 114 may be electrically coupled to the various hardware components of fluidics instrument 105. For example, controller 114 may be electrically coupled to microfluidics cartridge 110, thermal control electronics 118, magnets 120, GUI 122, and detection system 124. In particular, controller 114 may be electrically coupled to microfluidics cartridge 110 via cartridge interface 116, wherein cartridge interface 116 may be, for example, a pluggable interface for connecting mechanically and electrically to microfluidics cartridge 110.

Most chemical and biological processes have precise and stable temperature control for optimal efficiency and performance. Accordingly, thermal control electronics 118 may be any mechanisms for controlling the operating temperature of microfluidics cartridge 110. Thermal control electronics 118 may include, for example, any thermal sensors for controlling heaters (e.g., Peltier elements and resistive heaters). Thermal control electronics 118 may also include coolers arranged with respect to microfluidics cartridge 110.

Magnets 120 may be, for example, permanent magnets and/or electromagnets. In the case of electromagnets, controller 114 may be used to control the electromagnets 120. GUI 122 may be any type of digital display for conveying information to a user. In one example, GUI 122 may be the display of fluidics instrument 105. In another example, GUI 122 may be the display of any networked computing device connected to fluidics instrument 105 via a network. For example, a networked computer 132 may be connected to fluidics instrument 105 via a network 134.

Networked computer 132 may be, for example, any centralized server or cloud-based server. Network 134 may be, for example, a local area network (LAN) or wide area network (WAN) for connecting to the internet. The communications interface (not shown) of controller 114 may be any wired and/or wireless communication interface for connecting to a network (e.g., network 134). Information may be exchanged with other devices connected to the network. Though FIG. 1 shows a single networked computer 132, multiple computers (physical or virtual) may be connected in the microfluidics system 100 via network 134. For example, one computer may be used to control thermal control electronics 118. Then, another computer may be used to control electromagnets 120. Then, another computer that is optimized for storing information may be used to store data received from detection system 124. Then, yet another computer that is optimized for processing data may be used to process information received from fluidics instrument 105.

Controller 114 may, for example, be a general-purpose computer, special-purpose computer, personal computer, tablet device, smart phone, smart watch, mobile device, microprocessor, or other programmable data processing apparatus. Controller 114 may provide processing capabilities, such as storing, interpreting, and/or executing software instructions. Additionally, controller 114 may be used to control the overall operations of microfluidics system 100. The software instructions may comprise machine-readable code stored in non-transitory memory that is accessible by controller 114 for the execution of the instructions. Controller 114 may be configured and programmed to control data and/or power aspects of microfluidics system 100. Further, data storage (not shown) may be built into or provided separate from controller 114.

Further, in some embodiments, controller 114 may be external to fluidics instrument 105 (not shown in FIG. 1). The functions described above may be done remotely, for example via a mobile application running on a mobile device connected to various components (i.e., thermal controls electronics 118, among others) via a local network or other network. Output from detection system 124 may also be transmitted to an external controller 114 via such networks and displayed on a mobile application or another mobile app running on a mobile device specific for the external controller 114.

Generally, controller 114 may be used to manage any functions of microfluidics system 100. For example, controller 114 may be used to manage the operations of thermal control electronics 118, magnets 120, GUI 122, detection system 124, and any other instrumentation (not shown) in relation to microfluidics cartridge 110. Further, with respect to microfluidics cartridge 110, controller 114 may control droplet manipulation by activating/deactivating electrodes.

In other embodiments of microfluidics system 100, the functions of controller 114, thermal control electronics 118, magnets 120, GUI 122, detection system 124, and/or any other instrumentation may be integrated directly into microfluidics cartridge 110 rather than provided separately from microfluidics cartridge 110.

Detection system 124 may be, for example, an optical measurement system that includes an illumination source 126 and an optical measurement device 128. In this example, illumination source 126 and optical measurement device 128 may be arranged with respect to microfluidics cartridge 110

Digital Microfluidics Multi-Dynamic Range Parallel Assays

The disclosure provides methods that enable improved precision and linearity for digital microfluidics analyses (i.e., analyses performed on a droplet actuator using droplet operations), including for example, assays related to measuring analytes in a biological sample. Examples of assays that can be performed using a method of the disclosure include measuring analytes in blood, including analytes from blood components, such as analytes present in plasma. The disclosure provides a digital microfluidics device (or cartridge) and methods for performing a biochemical assay using the microfluidics device to measure an analyte in a sample.

The methods may generally include the use of digital microfluidic manipulation of multiple reaction droplets in parallel to generate a set of two or more separate reactions that can be used in an assay to quantify a target analyte. Each of the two or more reactions can be separately designed, "tuned" or "optimized" to cover a range of analyte concentrations that can be measured in a test sample, e.g., a high, low, or intermediate concentration range of the analyte. An assay-specific algorithm can then be used to compare the assay results produced from each reaction/standard curve and decide which reaction's result makes the most appropriate determination of the concentration of analyte in the sample, or whether a combination of the two or more results combined (e.g., using a weighted average) is most appropriate for determining the concentration of analyte in the sample.

The set of two or more separate reactions can be optimized or tuned, for example, for quantifying: (a) a relatively low concentration range of analyte in a sample, thereby enabling improved precision to the assay; and/or (b) a relatively high concentration range of analyte in a sample, thereby enabling greater linearity to the assay. In other embodiments one or more additional separate reactions can be used to optimize or tune for an intermediate concentration range of analyte. As used herein, the terms "relatively low concentration," "relatively high concentration," or "intermediate concentration," are all intended to be relative to one another. In other words, a relatively low concentration is a concentration that is lower than the relatively high concentration and the relatively high concentration is higher that the relatively low concentration. Similarly, an intermediate concentration comprises a concentration range that is between a relatively low concentration and a relatively high concentration.

In some embodiments, the methods can be used for biochemical assays that use a negative-slope standard curve for quantifying a target analyte in a sample, such as an enzyme inhibition assay. In accordance with various embodiments, the negative-slope standard curve can be a relatively high concentration range negative-slope standard curve, a relatively low concentration range negative-slope standard curve, or optionally, an intermediate concentration range negative-slope standard curve.

In some embodiments, the methods can be used for biochemical assays that use degradation of a target analyte to quantify the amount of analyte in a sample.

In one example, the methods can be used in an assay for measuring unbound bilirubin in a blood sample. As one of skill in the art would readily appreciate, high levels of unbound bilirubin can interfere with analyte detection, especially through absorbance-based detection means. As such, in accordance with the presently disclosed methods, in samples where bilirubin levels may be high (e.g., in a newborn baby or neonate), the use of a fluorescence-based substrate and a fluorescence-based assay reaction or protocol can be used. As used herein, a "high level of unbound bilirubin" is more than about 2 mg/dL, more than about 3 mg/dL, more than about 4 mg/dL, or more than about 5 mg/dL. Fluorescence-based assays and substrates may be particularly suited for assaying a sample from a newborn baby or neonate, where bilirubin levels are typically more than 2 mg/dL, whereas typical adult bilirubin levels are around 1 mg/dL.

In one embodiment, the disclosure provides methods for performing a fluorescence-based enzymatic assay for detection of an analyte. In another embodiment, the disclosure provides methods for performing a luminescence-based enzymatic assay or a chromogenic-based enzyme assay for detection of an analyte.

In one embodiment, the disclosure provides methods for performing a fluorescence-based enzymatic assay for measuring heparin levels in a blood sample.

Microfluidic Device

The disclosure provides a microfluidics device (or cartridge) configured for performing a biochemical assay.

FIG. 2 is a cross-sectional view illustrating an example of a portion of a microfluidics device 200 configured for performing a biochemical assay in droplets. Microfluidics device 200 includes a bottom substrate 210 and a top substrate 212 separated by a gap 214. In some embodiments top substrate 212 may be absent, and the methods of the disclosure may be carried out on a bottom substrate 210. A set of droplet operations electrodes 216, e.g., electrowetting electrodes, are arranged, for example, on bottom substrate 210. The droplet operations electrodes 116 are arranged for conducting droplet operations, such as droplet loading, dispensing, splitting, transporting, merging, and mixing. Gap 214 may be filled with a filler fluid 218. Filler fluid 218 can, for example, be a low-viscosity oil, such as silicone oil. In some cases, filler fluid 218 is absent, and the methods of the disclosure are carried out in air or in a gas environment. In some cases, both filler fluid 218 and top substrate 212 absent while conducting the methods of the disclosure.

An aqueous droplet 220 can be present in gap 214 of microfluidics device 200. In one example, droplet 220 is a droplet of a blood sample to be evaluated, such as a whole blood droplet or a plasma droplet. In another example, droplet 220 is a reagent droplet for conducting a biochemical assay. Oil filler fluid 218 fills gap 214 and surrounds droplet 220.

Multi-Dynamic Range Parallel Assays

The methods generally include the use of digital microfluidic manipulation of multiple reaction droplets in parallel to generate a set of two (2) or more separate reactions that can be used in a biochemical assay to quantify a target analyte. The set of two or more separate reactions can be optimized or tuned for quantifying: (a) a relatively low concentration range of analyte in a sample, thereby enabling improved precision to the assay; (b) a relatively high concentration range of analyte in a sample, thereby enabling greater linearity to the assay, or (c) an intermediate concentration range of an analyte in a sample.

Examples of parameters that can be used to optimize or tune a set of reactions used in an assay protocol for quantification of target analyte in a sample include, but are not limited to: (a) incubation time (e.g., the length of time a sample and/or certain reaction components are incubated prior to detecting an assay output); (b) concentration of one or more reagent components (e.g., the amount of enzyme used in an enzymatic reaction); and/or (c) dilution of the sample used in the assay.

As described above, in some embodiments the first reaction protocol is optimized for measuring a relatively high analyte concentration. In one embodiment, the first reaction protocol comprises a short incubation, wherein the sample and the enzyme/substrate reagent are incubated for a relatively short period of time. For example, in one embodiment, the short incubation period can be less than about 60 second. In another embodiment, the short incubation period can be from about 10 seconds to about 60 seconds, from about 30 seconds to about 60 seconds, or from about 45 seconds to about 60 seconds. In another embodiment, the first reaction protocol includes the use of a first reagent concentration, wherein the first reagent concentration is optimized for measuring a relatively high analyte concentration. For example, in one embodiment, the first reagent includes an enzyme reagent at a concentration of less than 0.5 U/mL. In another embodiment, the first reagent includes an enzyme reagent at a concentration of from about 0.01 U/mL to about 0.5 U/mL, from about 0.05 U/mL to about 0.5 U/mL, or from about 0.1 U/mL to about 0.5 U/mL.

As described above, in some embodiments the second reaction protocol is optimized for measuring a relatively low analyte concentration. In one embodiment, the second reaction protocol comprises a long incubation, wherein the sample and the enzyme/substrate reagent are incubated for a relatively long period of time. For example, in one embodiment, the long incubation period can be greater than about 60 second. In another embodiment, the long incubation period can be from about 60 seconds to about 240 seconds, from about 60 seconds to about 180 seconds, or from about 60 seconds to about 120 seconds. In another embodiment, the second reaction protocol includes the use of a second reagent concentration, wherein the second reagent concentration is optimized for measuring a relatively low analyte concentration. For example, in one embodiment, the second reagent includes an enzyme reagent at a concentration of greater than 0.5 U/mL. In another embodiment, the first reagent includes an enzyme reagent at a concentration of from about 0.5 U/mL to about 1.5 U/mL, from about 0.75 U/mL to about 1.5 U/mL, or from about 1.0 U/mL to about 1.5 U/mL.

In some embodiments, the methods can be used for conducting biochemical assays that use a negative-slope standard curve for quantifying a target analyte in a sample.

In one embodiment, the biochemical assay can be an enzyme inhibition assay. In an inhibitory assay, such as an enzyme inhibition assay, as the concentration of an analyte increases, the assay output signal decreases.

In one embodiment, the methods \ can be used in an enzyme inhibition assay for measuring heparin levels in a blood sample. In one example, an anti-factor Xa heparin assay (anti-FXa assay) can be performed on a digital microfluidics device using the methods of this disclosure.

Negative-Slope Standard Curves: Assay Precision and Linearity

It is useful to use a mathematical model to describe the relationship between precision and linearity in an assay that uses a negative-slope standard curve. For example, in an anti-FXa heparin assay a standard curve is used to quantify the amount of heparin in a test sample. The anti-FXa assay can, for example, be a fluorogenic assay that produces a positive kinetic fluorescence slope, with slope decreasing in proportion to the heparin concentration. During the assay, kinetic fluorescence data is collected which the instrument outputs as relative fluorescence units (RFU) over time data and a linear regression outputs the slope in RFU/msec. This slope value is typically consistent, with a 2-3% CV. The slope is then converted to analyte concentration (e.g., unfractionated heparin (UFH)) via a negative standard curve generated using samples with known analyte concentrations and RFUs.

FIG. 3 is a plot 300 showing an example of a standard curve 310 for determining heparin (UFH) concentration in a sample. Standard curve 310 has a negative slope, indicating that the assay signal (generated by enzyme activity) decreases with increasing heparin concentration (the inhibitor of the enzyme activity) in a sample. At a certain low concentration of analyte ([UFH]), signal measurements can be spread over a certain range, designated in plot 300 as σ. In the anti-FXa inhibition assay, a kinetic fluorescence slope can be quantified with good precision (about 2-3% CV), but due to the negative-slope standard curve, the good precision of the measured RFU/s may not carry over to good precision of the analyte concentration due to the propagation of error through the calculations involved in converting from RFU/s to analyte concentration.

In this example, a measure of the variance in the assay signal measurements (i.e., fluorescence signal generated by enzyme activity) can be described by the equation:

$$\text{Slope } CV = \frac{\sigma}{A}$$

and a measure of the variance between data points within the assay (i.e., assay output) can be described by the simplified equation:

$$\text{Assay } CV = \frac{\sigma}{B}$$

where the slope CV and the assay CV are proportional, but not 1:1 as they would be for a standard curve (positive slope) with a y intercept of 0. Further, due to the shallow slope of the negative standard curve, the precision of the measured assay signal (RFUs/ms) is worsened in conversion to analyte concentration [UFH]. This loss of precision in the measured assay signal in conversion to analyte concentration is a function of the standard curve's X-intercept, which is limited by a linearity requirement for performing the assay.

Provided the main sources of noise are inherent to the slope measurement (e.g. detection bias), and not inherent to the reaction's analyte concentration (e.g. poor sample mixing), a multiplicative factor can be used to translate from a slope CV to an assay CV. In the case of a positive-slope standard curve with an intercept of 0, the multiplicative factor is 1. However, in the case of a negative-slope standard curve, the multiplicative factor K becomes the ratio between the measured signal designated as "A" in plot 200 and the difference between the measured signal and the y-intercept, which is designated as "B" in plot 200. The conversion from a measured assay signal to analyte concentration can be described by the equation:

$$\text{Assay } CV = \text{Slope } CV * K$$

where $$K = \frac{A}{B}.$$

The multiplicative factor K is a function of the standard curve (i.e., K=f (standard curve)). To optimize an assay for precision, it is desirable to have K as low as possible to keep the slope CV from increasing as you calculate the assay CV. To keep the slope CV from increasing during calculation into assay CV, a standard curve with a steep negative slope would be required to effectively lower "A" (i.e., the spread of signal measurements (o) for samples) and increase "B" (i.e., the distance between the spread of signal measurements (o) for samples and the y-intercept value). This would effectively improve the assay measurements for analyte concentrations at the lower end of a concentration range. However, the improvement in assay measurements gained by potentially using a steeper standard curve for precision in measuring lower concentrations of analyte is offset by a loss in linearity, i.e., accurate quantification of the analyte at a relatively higher concentration in a sample. The present disclosure solves the issue of obtaining accuracy in a single instrument run for an analyte that could be present at either low or high concentration in a sample by providing multiple reactions on the microfluidic device, each reaction optimized for different concentration ranges (i.e., optimizing for precision and linearity).

In some embodiments, the methods can be used for a biochemical assay that uses a negative-slope standard curve for quantifying a target analyte in a sample. For example, two separate assay reactions can be performed on the microfluidic device, wherein one reaction is tuned for a lower concentration range and the other reaction is tuned for a higher concentration range. Accordingly, each reaction has its own standard curve which converts measured signal to an analyte concentration. An assay-specific algorithm can then be used to compare the assay results produced from each reaction/standard curve and decide which reaction produced the more appropriate determination of the concentration of analyte in the sample. In one example, an assay-specific algorithm for choosing between a calculation of analyte UFH in a reaction A and a reaction B, provides that if reaction B UFH calculation is <0.5 U/mL, use reaction A UFH calculation, otherwise use reaction B UFH calculation.

In some embodiments, the methods include a biochemical assay that uses a negative-slope standard curve for quantifying a target analyte in a sample. For example, a first standard curve can be used for quantifying a relatively low concentration of an analyte and a second standard curve can be used for quantifying a relatively high concentration of the analyte. Accordingly, two (2) separate assay reactions can be performed on the microfluidic device, wherein one reaction is optimized for the lower concentration range and the other reaction is optimized for the higher concentration range. An assay-specific algorithm can then be used to compare the assay results of the two standard curves and decide which standard curve is the most appropriate for determining the concentration of analyte in the sample. Alternatively, an algorithm could use both results together (i.e., rather than choosing one over another) to create a weighted average.

FIG. 4 is a plot 400 showing an example of two (2) separate standard curves tuned for quantification of a lower and a higher range of unfractionated heparin (UFH). In this example, the standard curves were tuned to low and high UFH concentration ranges by varying incubation time (i.e., the amount of time the sample and enzyme mix were incubated prior to addition of the enzyme substrate). For example, a short-incubation reaction was optimized for quantifying high heparin samples, while a long-incubation reaction was optimized for quantifying low heparin samples.

FIG. 5 is a flow diagram illustrating an example of a method 500 for determining an analyte level in a sample using the methods described herein. In this example, assay reagents (e.g., an enzyme reagent and/or a substrate reagent) are provided as dried reagent spots on the microfluidic device. Method 500 can include any or all the following steps as well as additional unspecified steps.

At a step 510, a sample (e.g., a blood sample or plasma sample) is loaded onto a microfluidic device. The sample can be whole blood, plasma or serum. For example, in one embodiment, a plasma sample can be prepared from a whole blood sample and loaded into a sample reservoir of the microfluidic device.

At a step 515, dried assay enzyme and substrate reagents are rehydrated. For example, a first droplet of diluent solution is dispensed from the diluent reservoir and used to rehydrate a dried enzyme reagent spot. A second droplet of diluent solution is dispensed from the diluent reservoir and used to rehydrate a substrate reagent spot (e.g., a dried fluorogenic analyte-specific substrate).

At a step 520, a first reaction protocol optimized for measuring a high analyte concentration is performed. For example, the first reaction protocol can be a short incubation reaction protocol or reaction protocol having a first substrate concentration, wherein the first reaction protocol is optimized for a high analyte concentration, and the second reaction protocol can be a long incubation reaction protocol or a reaction protocol having a second substrate concentration, wherein the second reaction protocol is optimized for a low analyte concentration. As described elsewhere herein, one or more additional reaction protocols can be used (e.g., a third reaction protocol, a fourth reaction protocol, etc.), wherein the one or more additional reaction protocols optimized for an intermediate analyte concentration.

As described above, in some embodiments the first reaction protocol is optimized for measuring a relatively high analyte concentration. In one embodiment, the first reaction protocol comprises a short incubation, wherein the sample and the enzyme/substrate reagent are incubated for a relatively short period of time. For example, in one embodiment, the short incubation period can be less than about 60 second. In another embodiment, the short incubation period can be from about 10 seconds to about 60 seconds, from about 30 seconds to about 60 seconds, or from about 45 seconds to about 60 seconds. In another embodiment, the first reaction protocol includes the use of a first reagent concentration, wherein the first reagent concentration is optimized for measuring a relatively high analyte concentration. For example, in one embodiment, the first reagent includes an enzyme reagent at a concentration of less than 0.5 U/mL. In another embodiment, the first reagent includes an enzyme reagent at a concentration of from about 0.01 U/mL to about 0.5 U/mL, from about 0.05 U/mL to about 0.5 U/mL, or from about 0.1 U/mL to about 0.5 U/mL.

As described above, in some embodiments the second reaction protocol is optimized for measuring a relatively low analyte concentration. In one embodiment, the second reaction protocol comprises a long incubation, wherein the sample and the enzyme/substrate reagent are incubated for a relatively long period of time. For example, in one embodiment, the long incubation period can be greater than about 60 second. In another embodiment, the long incubation period can be from about 60 seconds to about 240 seconds, from about 60 seconds to about 180 seconds, or from about 60 seconds to about 120 seconds. In another embodiment, the second reaction protocol includes the use of a second reagent concentration, wherein the second reagent concentration is optimized for measuring a relatively low analyte concentration. For example, in one embodiment, the second reagent includes an enzyme reagent at a concentration of greater than 0.5 U/mL. In another embodiment, the first reagent includes an enzyme reagent at a concentration of from about 0.5 U/mL to about 1.5 U/mL, from about 0.75 U/mL to about 1.5 U/mL, or from about 1.0 U/mL to about 1.5 U/mL.

In some embodiments, the first reaction protocol can include:

a. dispense a one (1) droplet unit (DU) (1DU) of plasma sample and transport to a reaction and detection zone;

b. dispense a 1DU of an enzyme reagent and merge with the IDU sample droplet to yield a 2DU first reaction droplet;

c. mix the 2DU first reaction droplet;

d. dispense a 1DU of the substrate reagent and combine with the 2DU first reaction droplet to yield a 3DU first detection droplet; and e. mix the 3DU first detection droplet and reading fluorescence kinetically.

At a step 525, optionally, a washing protocol can be performed to clean reaction and detection zone. For example, the washing protocol can include:

a. dispense four (4) 1DU of diluent and merge into two (2) 2DU diluent droplets;

b. transport a first 2DU droplet to the reaction and detection zone to clean the droplet operations electrodes; and c. transport the second 2DU diluent droplet to the reaction and detection zone to further clean the droplet operations electrodes.

At a step 530, a second reaction protocol optimized for measuring a low analyte concentration is performed. For example, the second reaction protocol can include:

a. dispense a 1 DU of plasma sample and merge with a 1DU of enzyme reagent to yield a 2DU second reaction droplet;

b. mix the 2DU long reaction droplet;

c. dispense a 1DU of the substrate reagent and combine with the 2DU second reaction droplet to yield a 3DU second detection droplet; and d. mix the 3DU second detection droplet and reading fluorescence kinetically.

At a step 535, the analyte concentration in the sample is determined or calculated. An assay-specific algorithm can be used to compare the assay results produced from each reaction/standard curve and a decision made as to which reaction, and which negative-slope standard curve, makes the most appropriate determination of the concentration of analyte in the sample.

For example, an analyte-specific algorithm can be used to calculate the concentration of the analyte using the high concentration range negative-slope standard curve, to calculate the concentration of the analyte using the low concentration range negative-slope standard curve, and/or, optionally, to calculate the concentration of the analyte using the intermediate concentration range negative-slope standard curve and the most appropriate concentration determined. In another embodiment, a combination of the two or more results can be combined, e.g., via a weighted average, to determine the concentration of analyte in the sample.

Heparin Monitoring Assay

In one aspect, the disclosure provides a microfluidic device and methods configured for monitoring heparin levels in a blood sample. Heparin (e.g., unfractionated heparin (UFH) or low molecular weight heparin (LMWH)) is an anticoagulant that may be used in an antithrombotic therapy. The therapeutic range for unfractionated heparin is typically 0.3-0.7 IU/mL. The therapeutic range for low molecular weight heparin (LMWH) can range from 0.5-1.2 IU/mL. The exact dosage of heparin administered during therapy is critical and should be closely monitored to avoid either excessive bleeding or clotting.

In some instances, the disclosure makes use of an anti-Factor Xa ("anti-FXa") assay to measure and monitor heparin levels in a plasma sample. Heparin's antithrombotic properties are mediated through its interaction with anti-thrombin (AT), activated Factor X (FXa), and thrombin. When heparin and antithrombin are complexed, antithrombin binds FXa. Antithrombin-bound FXa is inactivated and will not participate in the coagulation cascade or in the anti-FXa assay, substrate cleavage. The anti-FXa assay is a functional enzymatic assay that measures the inhibition of clotting factor Xa by heparin-bound antithrombin (AT), which reflects the heparin concentration in the plasma sample. The anti-FXa assay generally includes: (1) combining a plasma sample droplet with an FXa enzyme reagent droplet; (2) merging the combined plasma-enzyme reagent droplet with an FXa-specific substrate droplet; and (3) detecting the product of the enzymatic conversion of the FXa-specific substrate. Sometimes, step (1) and step (2) can be reversed.

In one embodiment, the anti-FXa assay can be used to measure unfractionated heparin (UFH) in a plasma sample.

In one embodiment, the anti-FXa assay can be used to measure low molecular weight heparin (LMWH) in a plasma sample.

In one embodiment, the plasma sample can be prepared on the microfluidic device from a whole blood sample. For example, a plasma sample can be prepared on the microfluidic device from a whole blood sample by combining a whole blood sample droplet with an agglutination reagent droplet and separating a plasma fraction from a red blood cell fraction using a plasma separation process. In one example, the agglutination reagent can be a hemagglutinating lectin (e.g., SGL or "potato lectin"). Another agglutination reagent that could be used is *Phaseolus vulgaris* lectin E (PHAE).

In one embodiment, the plasma sample can be prepared on-bench prior to loading onto the microfluidic device.

FIG. 6 is a schematic diagram illustrating an example of an arrangement of droplet operations electrodes 600 configured for conducting an anti-FXa assay for heparin monitoring on a microfluidic device. The arrangement of droplet operations electrodes 600 includes a diluent reservoir 610 for dispensing a diluent solution and one or more reagent reservoirs 615 for dispensing assay reagents (e.g., a first assay reagent R1, a second assay reagent R2, and a third assay reagent R3); and a sample reservoir 625 for loading and dispensing a blood sample. Although, in this example, the reagents are "dry" reagents, "wet" reagents could also be used to similar effect. The arrangement of droplet operations electrodes 600 can also include a reaction and detection zone for performing a fluidic anti-FXa assay protocol. In this example, incubation (enzyme+sample) occurs in the center loop, which is the 4-electrode-tall, 7-electrode-wide rectangle centered above R3 on the diagram. Reaction (enzyme+sample+substrate) and detection both occur in the right loop, which is the 4×8 rectangle whose left edge lines up with R1 on the diagram. An example of a fluidic assay anti-FXa protocol is described in more detail with reference to FIG. 7-8.

In some embodiments, one or more assay reagents can be provided as dried reagent spots on certain droplet operations electrodes 600. For example, a first assay reagent R1 (e.g., an FXa enzyme reagent) can be provided as a dried reagent spot on one or more droplet operations electrode arranged in a line or path with a first reagent reservoir 615; and a second assay reagent R2 (e.g., an FXa-specific substrate reagent) can be provided as a dried reagent spot on one or more droplet operations electrode arranged in a line or path with a second reagent reservoir 615. In some embodiments, a third assay reagent R3, i.e., a hemagglutinating lectin (e.g., SGL or "potato lectin") can be provided as a dried reagent spot on one or more droplet operations electrodes arranged in a line or path with a third reagent reservoir 615. The dried reagents are then rehydrated using, for example, the diluent solution provided in diluent reservoir 610 prior to conducting the assay.

In one embodiment, the FXa-specific substrate is a chromogenic substrate. In one example, the chromogenic substrate is SPECTROZYME FXa (BioMedica Diagnostics (Windsor, NS Canada)).

In one embodiment, the FXa-specific substrate is a fluorogenic substrate. In one example, the fluorogenic substrate is SPECTROFLUOR FXa (BioMedica Diagnostics (Windsor, NS Canada))

FIG. 7 is a flow diagram illustrating an example of a method 700 for measuring heparin in a plasma sample using an anti-FXa assay on a microfluidic device. In this example, assay reagents (i.e., FXa enzyme reagent and FXa-specific substrate reagent) are provided as dried reagent spots on the microfluidic device. Method 700 can include any or all the following steps as well as additional unspecified steps.

At a step 710, a plasma sample is loaded onto a microfluidic device. For example, a plasma sample prepared on-bench from a whole blood sample is diluted 1:6 and loaded into a sample reservoir of the microfluidic device.

At a step 715, dried assay enzyme and substrate reagents are rehydrated. For example, a first droplet of diluent solution is dispensed from the diluent reservoir and used to rehydrate a dried FXa enzyme reagent spot. A second droplet of diluent solution is dispensed from the diluent reservoir and used to rehydrate a dried fluorogenic FXa-specific substrate reagent spot.

At a step 720, a short reaction protocol for measuring high heparin levels is performed. For example, the short reaction protocol can include:

a. dispense a one (1) droplet unit (DU) (1DU) of plasma sample and transport to a reaction and detection zone;

b. dispense a 1DU of FXa enzyme reagent and merge with the 1DU plasma sample droplet to yield a 2DU short reaction droplet;

c. mix the 2DU short reaction droplet and incubating the reaction mixture for a short incubation time (e.g., for about thirty (30) seconds to about sixty (60) seconds);

d. dispense a 1DU of the fluorogenic FXa-specific substrate reagent and combine with the 2DU short reaction droplet to yield a 3DU short detection droplet; and e. mix the 3DU short detection droplet and reading fluorescence kinetically.

At a step 725, a washing protocol is performed to clean reaction and detection zone. For example, the washing protocol can include:

a. dispense four (4) 1DU of diluent and merge into two (2) 2DU diluent droplets;

b. transport a first 2DU droplet to the reaction and detection zone to clean the droplet operations electrodes; and c. transport the second 2DU diluent droplet to the reaction and detection zone to further clean the droplet operations electrodes.

At a step 730, a long reaction protocol for measuring low heparin levels is performed. For example, the long reaction protocol can include:

a. dispense a 1 DU of plasma sample and merge with a 1DU of FXa enzyme reagent to yield a 2DU long reaction droplet;

b. mix the 2DU long reaction droplet and incubating the reaction mixture for a short incubation time (e.g., for about ninety (00) seconds to about one-hundred and twenty (120) seconds);

c. dispense a 1DU of the fluorogenic FXa-specific substrate reagent and combine with the 2DU long reaction droplet to yield a 3DU long detection droplet; and d. mix the 3DU long detection droplet and reading fluorescence kinetically.

At a step 735, the heparin concentration in the test plasma sample is calculated. For example, an anti-FXa specific algorithm can be used to compare the short and long reaction assay results (each determined from their appropriate standard curves) and decide which reaction is better suited for determining the concentration of heparin in the plasma sample. For example, calculating the amount of heparin in the plasma sample can include:

a. providing two or more data sets of known heparin concentrations and corresponding relative fluorescence values;

b. performing a linear regression analysis using the data set of known heparin concentrations and their corresponding relative fluorescence values to generate two (2) or more standard curves; and c. using the plasma relative fluorescence measurements and the linear regression slope and intercept values of the standard curves to calculate the amount of heparin in the test plasma sample.

In one embodiment, an analyte-specific algorithm can be used to calculate the concentration of the analyte using the high concentration range negative-slope standard curve, to calculate the concentration of the analyte using the low concentration range negative-slope standard curve, and/or, optionally, to calculate the concentration of the analyte using the intermediate concentration range negative-slope standard curve and the most appropriate concentration determined. In another embodiment, a combination of the two or more results can be combined, e.g., via a weighted average, to determine the concentration of analyte in the sample.

FIG. 8 is a flow diagram illustrating an example of a method 800 for measuring heparin in a plasma sample using an anti-FXa assay on a microfluidic device. In this example, assay reagents (i.e., FXa enzyme reagent and FXa-specific substrate reagent) are provided as dried reagent spots on the microfluidic device. Method 700 can include any or all the following steps as well as additional unspecified steps.

At a step 810, a plasma sample is loaded onto a microfluidic device. For example, a plasma sample prepared on-bench from a whole blood sample is diluted 1:6 and loaded into a sample reservoir of the microfluidic device.

At a step 815, dried assay enzyme and substrate reagents are rehydrated. For example, a first droplet of diluent solution is dispensed from the diluent reservoir and used to rehydrate a dried FXa enzyme reagent spot. A second droplet of diluent solution is dispensed from the diluent reservoir and used to rehydrate a dried fluorogenic FXa-specific substrate reagent spot.

At a step 820, a first reaction protocol can be used, wherein the first reaction protocol is optimized for measuring high heparin levels. For example, the first reaction protocol can include:

a. dispense a one (1) droplet unit (DU) (1DU) of plasma sample and transport to a reaction and detection zone;

b. dispense a 1DU of a first FXa enzyme reagent at a first concentration (e.g., from about 0.01 U/mL to about 0.5 U/mL) optimized for measuring high heparin levels and merge with the 1DU plasma sample droplet to yield a 2DU first reaction droplet;

c. mix the 2DU first reaction droplet;

d. dispense a 1DU of the fluorogenic FXa-specific substrate reagent and combine with the 2DU first reaction droplet to yield a 3DU first detection droplet; and e. mix the 3DU first detection droplet and reading fluorescence kinetically.

At a step 825, optionally, a washing protocol is performed to clean reaction and detection zone. For example, the washing protocol can include:

a. dispense four (4) 1DU of diluent and merge into two (2) 2DU diluent droplets;

b. transport a first 2DU droplet to the reaction and detection zone to clean the droplet operations electrodes; and c. transport the second 2DU diluent droplet to the reaction and detection zone to further clean the droplet operations electrodes.

At a step 830, a second reaction protocol for measuring low heparin levels is performed. For example, the long reaction protocol can include:

a. dispending a 1DU of a second FXa enzyme reagent at a second concentration (e.g., from about 0.5 U/mL to about 1.5 U/mL) optimized for measuring low heparin levels and merge with the 1DU plasma sample droplet to yield a 2DU second reaction droplet b. mix the 2DU second reaction droplet;

c. dispense a 1DU of the fluorogenic FXa-specific substrate reagent and combine with the 2DU second reaction droplet to yield a 3DU second detection droplet; and d. mix the 3DU second detection droplet and reading fluorescence kinetically.

At a step 835, the heparin concentration in the test plasma sample is calculated. For example, an anti-FXa specific algorithm can be used to compare the first and second reaction assay results (each determined from their appropriate standard curves) and decide which reaction is better suited for determining the concentration of heparin in the plasma sample. For example, calculating the amount of heparin in the plasma sample can include:

a. providing two or more data sets of known heparin concentrations and corresponding relative fluorescence values;

b. performing a linear regression analysis using the data set of known heparin concentrations and their corresponding relative fluorescence values to generate two (2) or more standard curves; and c. using the plasma relative fluorescence measurements and the linear regression slope and intercept values of the standard curves to calculate the amount of heparin in the test plasma sample.

In one embodiment, an analyte-specific algorithm can be used to calculate the concentration of the analyte using the high concentration range negative-slope standard curve, to calculate the concentration of the analyte using the low concentration range negative-slope standard curve, and/or, optionally, to calculate the concentration of the analyte using the intermediate concentration range negative-slope standard curve and the most appropriate concentration determined. In another embodiment, a combination of the two or more results can be combined, e.g., via a weighted average, to determine the concentration of analyte in the sample.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," "comprising," "include," "includes," and "including," are intended to be non-limiting, such that recitation of items in a list is not to the exclusion of other like items that may be substituted or added to the listed items.

Terms like "preferably," "commonly," and "typically" are not utilized herein to limit the scope of the claimed embodiments or to imply that certain features are critical or essential to the structure or function of the claimed embodiments. These terms are intended to highlight alternative or additional features that may or may not be utilized in a particular embodiment of the present disclosure.

The term "substantially" is utilized herein to represent the inherent degree of uncertainty that may be attributed to any quantitative comparison, value, measurement, or other representation and to represent the degree by which a quantitative representation may vary from a stated reference without resulting in a change in the basic function of the subject matter at issue.

Various modifications and variations of the disclosed methods, compositions, and uses of this disclosure will be apparent to the skilled person without departing from the scope and spirit of the methods and systems described herein. Although the methods and systems have been disclosed in connection with specific preferred aspects or embodiments, the methods and systems as claimed should not be unduly limited to such specific aspects or embodiments.

The presently disclosed methods may be implemented using hardware, software, or a combination thereof and may be implemented in one or more computer systems or other processing systems.

In one aspect, the methods and systems described herein are directed toward one or more computer systems capable of carrying out the functionality described herein.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount, or range. Accordingly, unless indicated to the contrary, the numerical parameters set forth in the following specification and attached claims are not and need not be exact but may be approximate and/or larger or smaller as desired, reflecting tolerances, conversion factors, rounding off, measurement error and the like, and other factors known to those of skill in the art depending on the desired properties sought to be obtained by the presently disclosed subject matter.

For example, the term "about," when referring to a value can be meant to encompass variations of, in some embodiments ±100%, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Unless specifically stated otherwise, terms such as "receiving," "routing," "updating," "providing," or the like, refer to actions and processes performed or implemented by computing devices that manipulates and transforms data represented as physical (electronic) quantities within the computing device's registers and memories into other data similarly represented as physical quantities within the computing device memories or registers or other such information storage, transmission or display devices. Also, the terms "first," "second," "third," "fourth," etc., as used herein are meant as labels to distinguish among different elements and may not necessarily have an ordinal meaning according to their numerical designation.

Examples described herein also relate to an apparatus for performing the operations described herein. This apparatus may be specially constructed for the required purposes, or it may comprise a general-purpose computing device selectively programmed by a computer program stored in the computing device. Such a computer program may be stored in a computer-readable non-transitory storage medium.

The methods and illustrative examples described herein are not inherently related to any particular computer or other apparatus. Various general-purpose systems may be used in accordance with the teachings described herein, or it may prove convenient to construct more specialized apparatus to perform the required method steps. The required structure for a variety of these systems will appear as set forth in the description above.

It should also be noted that in some alternative implementations, the functions/acts noted may occur out of the order noted in the figures. For example, two (2) figures shown in succession may in fact be executed substantially concurrently or may sometimes be executed in the reverse order, depending upon the functionality/acts involved.

Although the method operations were described in a specific order, other operations may be performed in between described operations, described operations may be adjusted so that they occur at slightly different times, or the described operations may be distributed in a system which allows the occurrence of the processing operations at various intervals associated with the processing.

Various units, circuits, or other components may be described or claimed as "configured to" or "configurable to" perform a task or tasks. In such contexts, the phrase "configured to" or "configurable to" is used to connote structure by indicating that the units/circuits/components include structure (e.g., circuitry) that performs the task or tasks during operation. As such, the unit/circuit/component can be said to be configured to perform the task, or configurable to perform the task, even when the specified unit/circuit/component is not currently operational (e.g., is not on).

The units/circuits/components used with the "configured to" or "configurable to" language include hardware—for example, circuits, memory storing program instructions executable to implement the operation, etc. Reciting that a unit/circuit/component is "configured to" perform one or more tasks, or is "configurable to" perform one or more tasks, is expressly intended not to invoke 35 U.S.C. 112, sixth paragraph, for that unit/circuit/component.

Additionally, "configured to" or "configurable to" can include generic structure (e.g., generic circuitry) that is manipulated by software and/or firmware (e.g., an FPGA or a general-purpose processor executing software) to operate in manner that can perform the task(s) at issue. "Configured to" may also include adapting a manufacturing process (e.g., a semiconductor fabrication facility) to fabricate devices (e.g., integrated circuits) that are adapted to implement or perform one or more tasks. "Configurable to" is expressly intended not to apply to blank media, an unprogrammed processor or unprogrammed generic computer, or an unprogrammed programmable logic device, programmable gate array, or other unprogrammed device, unless accompanied by programmed media that confers the ability to the unprogrammed device to be configured to perform the disclosed function(s).

Although the foregoing subject matter has been described in some detail by way of illustration and example for purposes of clarity of understanding, it will be understood by those skilled in the art that certain changes and modifications can be practiced within the scope of the appended claims.

We claim:

1. A method for assaying analytes on a microfluidic device, the method comprising:

a. loading a sample comprising an analyte to be assayed onto a microfluidic device;

b. performing a short-incubation reaction protocol to measure a relatively high concentration of the analyte, the short-incubation reaction protocol comprising merging a first droplet of the sample with one or more reaction reagents, wherein the short-incubation reaction protocol is optimized to measure a relatively high concentration of the analyte, and wherein a first relatively high concentration range negative-slope standard curve is used for quantifying the analyte;

c. performing a long incubation reaction protocol to measure a relatively low concentration of the analyte, the long incubation reaction protocol comprising merging a second droplet of the sample with the one or more reaction reagents, wherein the long incubation reaction protocol is optimized to measure a relatively low concentration of the analyte, and wherein a second relatively low concentration range negative-slope standard curve is used for quantifying the analyte;

d. optionally, performing an intermediate incubation reaction protocol to measure an intermediate concentration of the analyte, the intermediate incubation reaction protocol comprising merging a third droplet of the sample with one or more reaction reagents, wherein the intermediate reaction protocol is optimized to measure an intermediate concentration of the analyte, and wherein a third intermediate concentration range negative-slope standard curve is used for quantifying the analyte; and e. calculating a concentration of the analyte using the high concentration range negative-slope standard curve, the low concentration range negative-slope standard curve, and/or optionally the intermediate negative-slope standard curve.

2. The method of claim 1, wherein calculating the concentration of the analyte comprises comparing the calculated concentration of the analyte from the high concentration range negative-slope standard curve and the calculated concentration of the analyte from the low concentration range negative-slope standard curve, and optionally the calculated concentration of the analyte from the intermediate negative-slope standard curve.

3. The method of claim 2, wherein the calculated concentrations from the high concentration range negative-slope standard curve, from the low concentration range negative-slope standard curve, and optionally from the calculated concentration of the analyte from the intermediate negative-slope standard curve, are combined using weighted averages.

4. The method of claim 1, wherein the protocols of the assay comprises an enzyme inhibition assay wherein the measured signal decreases as the concentration of the analyte increases.

5. The method of claim 1, wherein the protocols of the assay comprise an assay for degradation of the analyte.

6. The method of claim 1, wherein the sample is whole blood, plasma or serum.

7. The method of claim 1, wherein the sample is a blood sample and a plasma sample is prepared from the whole blood sample on the microfluidic device.

8. The method of claim 7, wherein the preparing comprises combining a whole blood sample droplet with an agglutination reagent and separating a plasma fraction from a red blood cell fraction using a plasma separation process.

9. The method of claim 8, wherein the plasma sample is prepared from the whole blood sample prior to loading onto the microfluidic device.

10. The method of claim 1, wherein the one or more reaction reagents includes an analyte-specific substrate, and wherein the substrate is a chromogenic substrate or a fluorogenic substrate.

11. The method of claim 10, wherein the protocols of the assay comprise an absorbance-based assay, a luminescence-based assay and/or a fluorescence-based assay.

12. The method of claim 1, wherein the sample is a whole blood sample, the protocols of the assay comprise an enzyme inhibition assay, and the analyte is heparin.

13. The method of claim 12, wherein the one or more reaction reagents comprises an FXa enzyme reagent and an FXa-specific substrate, and wherein a plasma sample droplet from the whole blood sample is (1) merged with the FXa enzyme reagent and then (2) the combined blood sample-enzyme reagent droplet is merged with the FXa-specific substrate, or wherein step (1) and step (2) are reversed.

14. The method of claim 13, wherein the FXa-specific substrate is a chromogenic substrate, a luminescence substrate, or a fluorogenic substrate and wherein the protocols of the assay comprise an absorbance-based assay, a luminescence-based assay, or a fluorescence-based assay.

15. The method of claim 12, wherein the heparin is unfractionated heparin (UFH) or low molecular weight heparin (LMWH).

16. The method of claim 13, wherein performing the short-incubation reaction protocol comprises:

a. dispensing a one (1) droplet unit (DU) (1DU) of the plasma sample and transporting it to a reaction and detection zone;

b. dispensing a 1DU of the FXa enzyme reagent and merging it with the IDU plasma sample droplet to yield a 2DU short reaction droplet;

c. mixing the 2DU short reaction droplet;

d. dispensing a 1DU of the fluorogenic FXa-specific substrate reagent and combining it with the 2DU short reaction droplet to yield a 3DU short detection droplet; and e. mixing the 3DU short detection droplet and reading relative activity units over time as a measured signal for the short-incubation reaction.

17. The method of claim 16, further comprising performing a washing protocol to clean the reaction and detection zone, and wherein the long-incubation reaction protocol comprises:

a. dispensing a 1 DU of the plasma sample and merging it with a 1DU of FXa enzyme reagent to yield a 2DU long reaction droplet;

b. mixing the 2DU long reaction droplet;

c. dispensing a 1DU of the fluorogenic FXa-specific substrate reagent and combining it with the 2DU long reaction droplet to yield a 3DU long detection droplet; and d. mixing the 3DU long detection droplet and reading relative activity units over time as the measured signal for the long-incubation reaction.

18. The method of claim 1, wherein the sample is a blood sample, the protocols of the assay comprise an assay for degradation of the analyte, and the analyte is unbound bilirubin.

19. The method of claim 1 wherein the microfluidic device comprises an electrowetting cartridge and the loading, merging, combining, dispensing, and/or initiating is performed using electrowetting-mediated droplet operations.

20. The method of claim 1, wherein the incubation reactions are individually tuned to improve one or both precision and linearity in the assay.

21. The method of claim 20, wherein tuning comprises optimizing one or a combination of: (a) length of the incubation reaction; (b) a concentration of one or more of the reagents; and (c) a dilution of the sample.

22. The method of claim 1, wherein the incubation reactions are run in parallel on the microfluidic device or run one after the other on the microfluidic device.

23. The method of claim 1, wherein the incubation reactions are performed in a reaction and detection zone on the microfluidic device, the method further comprising performing a washing protocol to clean the reaction and detection zones between incubation reactions.

24. The method of claim 1, wherein one or more of the reaction reagents is provided as a dried reagent spot on one or more droplet operations electrodes on the microfluidic device.

25. The method of claim 24, wherein the one or more dried reagent spots are rehydrated using a diluent solution provided in a diluent reservoir.

26. The method of any claim 1, wherein the short-incubation reaction protocol comprises an incubation period of less than about sixty (60) seconds.

27. The method of claim 1, wherein the long incubation reaction protocol comprises an incubation period of more than about sixty (60) seconds.

28. The method of claim 1, wherein the sample is a blood sample having an unbound bilirubin level of more than 2 mg/dL, the analyte-specific substrate is a fluorogenic substrate and the assay is a fluorescence-based assay.

29. The method of claim 28, wherein the blood sample is from neonate.

* * * * *